US00PP18214P2

(12) United States Plant Patent
Kaagman

(10) Patent No.: US PP18,214 P2
(45) Date of Patent: Nov. 13, 2007

(54) ***CAMPANULA* PLANT NAMED 'CAMP TRAILBULE'**

(50) Latin Name: ***Campanula* hybrid**
Varietal Denomination: Camp Trailbule

(75) Inventor: Pim Kaagman, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 11/412,516

(22) Filed: Apr. 27, 2006

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

GTITM UPOVROM Citation for 'Camp Trailbulr' as per QZ PBR 20050111; filed Jan. 24, 2005.*

* cited by examiner

*Primary Examiner*—Kent Bell
(74) *Attorney, Agent, or Firm*—Jondle & Associates, P.C.

(57) ABSTRACT

A new *campanula* plant particularly distinguished by large, wide open, blue-violet, star-shaped flowers, medium-green foliage with somewhat fleshy, cordate leaves, good-branching ability, compact, spreading to prostrate and somewhat trailing plant habit, is disclosed.

2 Drawing Sheets

Genus and species: *Campanula* hybrid.
Variety denomination: 'Camp Trailbule'.

BACKGROUND OF THE NEW PLANT

The present invention comprises a new and distinct cultivar of *campanula,* botanically known as *Campanula* hybrid, and hereinafter referred to by the cultivar name 'Camp Trailbule'. The new cultivar originated from a hybridization made in February 1999 in Andijk, The Netherlands. The female parent was 'CD-20-1', a proprietary (unpatented) blue-flowered *Campanula isophylla* plant, while the male parent was 'CH-60-5', a proprietary (unpatented) blue-flowered *Campanula fragilis* plant. The seeds produced by the hybridization were shown in August 1999, and the resulting seedlings were selected in January 2000. A single plant selection was chosen for further evaluation and for asexual propagation in 2000.

The new cultivar was created in 1999 in Andijk, The Netherlands and has been asexually reproduced repeatedly by vegetative cuttings and tissue culture in Andijk, The Netherlands over a five-year period. 'Camp Trailbule' has also been trialed at Hillscheid, Germany. The present invention has been found to retain its distinctive characteristics through successive asexual propagations.

Plant Breeder's Rights for this cultivar were applied for in Canada on Mar. 21, 2006 and with the European Union on Jan. 24, 2005.

SUMMARY OF THE INVENTION

The following are the most outstanding and distinguishing characteristics of this new cultivar when grown under normal horticultural practices in Andijk, The Netherlands and Hillscheid, Germany.

1. Large, wide-open, blue-violet, star-shaped flowers;
2. Medium-green foliage with somewhat fleshy, cordate leaves;

3. Good branching ability;
4. Relatively compact and tight growth; and
5. A spreading to prostrate and somewhat trailing plant habit.

DESCRIPTION OF PHOTOGRAPHS

This new *campanula* plant is illustrated by the accompanying photographs which show overall plant habit including blooms, buds, and foliage of the plant; the colors shown are as true as can be reasonably obtained by conventional photographic procedures. The photographs are of 7-month-old plants grown in a greenhouse in Andijk, The Netherlands in May 2003.

DESCRIPTION OF THE NEW CULTIVAR

Figure 1:
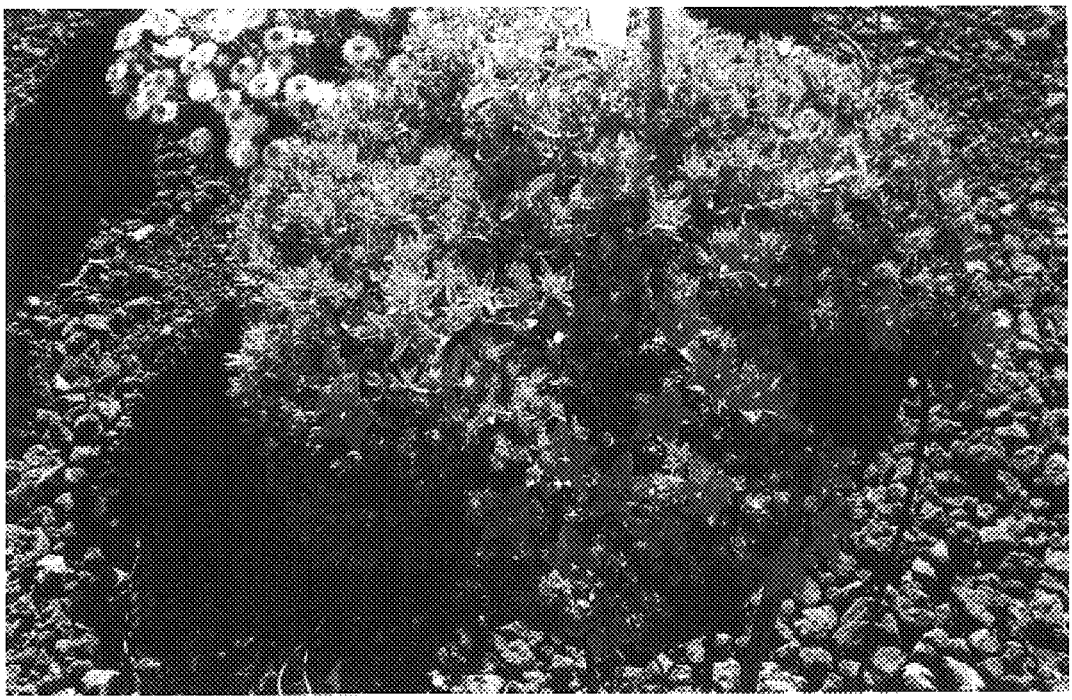
FIG. 1 shows the overall plant habit, including blooms, buds, foliage and plant habit.
Figure 2:
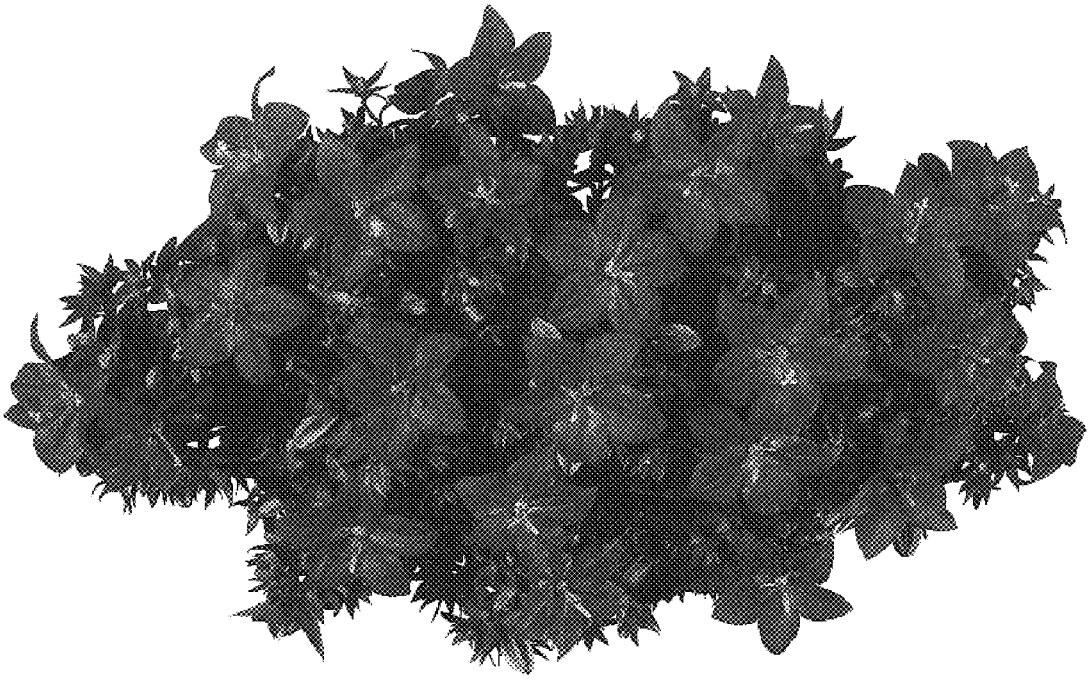
FIG. 2 shows a close-up of the mature inflorescences.

The following detailed description sets forth the distinctive characteristics of 'Camp Trailbule'. The data which define these characteristics were collected from asexual reproductions carried out in Andijk, The Netherlands. The plant history was taken partly on 5-week old plants, still in a vegetative state and grown in Hillscheid, Germany in the spring of 2006. Rooted cuttings were planted in 10.5-cm pots and grown in a greenhouse. The plants were not pinched. Flower observations were made on 35-week-old plants in fall of 2005. Color readings were taken under natural light. Color references are primarily to The R.H.S. Colour Chart of The Royal Horticultural Society of London (R.H.S.) (2001).

DETAILED BOTANICAL DESCRIPTION

Classification:
*Family.*—Campanulaceae.
*Botanical.*—*Campanula* hybrid.
*Common name.*—Bellflower.

Parentage:

*Female parent.*—'CD-20-1', a proprietary (unpatented) blue-flowered *Campanula isophylla* plant.

*Male parent.*—'CH-60-5', a proprietary (unpatented) blue-flowered *Campanula fragilis* plant.

Growth:

*Form.*—Herbaceous perennial; for commercial purposes the variety can be cultivated as an annual.

*Habit.*—Initially spreading, later decumbent and somewhat trailing plant habit, well-branching; pinching results in a more even plant habit.

*Height* (*measured from the top of the soil*).—8 cm.

*Width* (*horizontal plant diameter*).—12 cm.

*Propagation.*—Terminal tips for cutting.

*Time to produce a finished flowering plant.*—13 to 15 weeks for a 10 cm to 12 cm pot.

*Outdoor plant performance.*—As flowering pot plants, for small hanging-baskets.

*Time to initiate and develop roots.*—25 days.

*Root description.*—Fibrous, fine and cream-white.

Stems:

*Average number* (*per plant*).—8 to 12.

*Length.*—6 cm to 8 cm.

*Diameter* (*at midpoint*).—0.3 cm to 0.4 cm.

*Internode length.*—0.5 cm to 1.2 cm.

*Color.*—RHS 137D to RHS 138A (green).

*Anthocyanin.*—None.

*Texture.*—Dense pubescence.

Leaves:

*Arrangement.*—Alternate.

*Size.*—Length: Up to 3.0 cm. Width: 2.8 cm. Shape: Mostly cordate, smaller, leaves at flowering stems may be ovate or even lanceolate.

*Margin.*—Serrated or with few notches.

*Apex.*—Obtuse to rounded.

*Base.*—Cordate.

*Color.*—Immature leaves: Upper surface: RHS 143A. Lower surface: RHS 143B. Mature leaves: Upper surface: RHS 137A. Lower surface: RHS 138A.

*Texture.*—Velvety, with fine pubescence on the upper surface and bristle-like hair on the veins of the lower surface and along the margins.

*Venation.*—Pinnate.

*Venation color.*—RHS 145A.

*Petioles.*—Length: 0.5 cm to 2.5 cm. Width: 1.0 cm to 1.5 cm. Color: RHS 137C. Texture: Covered with dense pubescence.

Flower bud:

*Shape.*—Narrow and oval (elongated) with furrows.

*Size.*—Length: 1.5 cm. Diameter: 0.7 cm.

*Color at tight bud.*—RHS 85B to RHS 85D (light-blue) and RHS 145C (pale-green).

Inflorescence:

*Blooming habit.*—Continuous under long-day conditions.

*Inflorescence type.*—Terminal, bending and decumbent.

*Number of flowers per inflorescence.*—About 7 to 10 flowers and buds.

*Lastingness of individual blooms on the plant.*—About 14 days.

*Fragrance.*—None.

*Length.*—5.5 cm to 6.5 cm.

*Diameter.*—Up to 4.0 cm.

*Peduncle.*—Length: 5.0 cm. Diameter: 0.2 cm. Color: RHS 138A. Texture: Dense pubescence.

*Pedicels.*—Length: 0.5 cm to 1.0 cm. Diameter: 0.1 cm. Color: RHS 143B (green). Anthocyanin: None. Texture: Appears smooth, nearly glabrous.

Flowers:

*Flower type.*—Single, actinomorphic; campanulate.

*Corolla.*—Shape: Round, wide open cup-shape; composed of 5 petals partly fused with lobes opening outward. Size: Diameter: 3.5 cm to 4.3 cm. Depth: 0.8 cm. Color: Upper surface: RHS N87B at the lobes and somewhat paler blue in the middle of the flower. Lower surface: RHS 85B. Inside: RHS 85B.

*Petals.*—Shape: Ovate. Size: Length: 1.4 cm. Width: 1.2 cm. Quantity: 5. Apex: Acute to obtuse. Base: Fused. Margin: Entire. Texture: Smooth, glabrous, apart from a few hairs at the tip of lower surface.

*Calyx.*—Composed of 5 sepals fused at the base.

*Sepals.*—Number: 5. Color: Upper surface: RHS 137A (deep-green). Lower surface: RHS 137C. Length: 0.9 cm. Width: 0.3 cm. Shape: Lanceolate, initially horizontal, later downwards directed. Apex: Acute. Base: Fused. Margin: Entire. Texture: Short pubescence mostly at the margins.

Reproductive organs:

*Stamens.*—Quantity: 5, with the bases coherent, enclosing the upper part of the ovary. Filament color: RHS N155A. Filament length: 0.5 cm. Filament diameter: 0.3 cm at the base and 0.1 cm below the stamen. Anther color: RHS 163B (ochre). Anther size: Length: 0.4 cm. Diameter: 0.1 cm. Pollen color: RHS 162B (yellowish). Pollen amount: Sparse.

*Pistil.*—Quantity: 1. Length: 1.4 cm. Stigma color: RHS 157D. Stigma shape: 3-lobed with brush-like-arranged hair below the stigma. Style color: Upper part: RHS 91A (light-blue). Base: RHS N155A (white). Style length: 1.1 cm.

*Ovary.*—Type: Intermediate position. Shape: Oval to nearly round. Length: 0.4 cm. Diameter: 0.3 cm to 0.4 cm. Color: RHS 145A (pale-green).

Fruit and seed set: None observed.

Disease and insect resistance: No special observations made.

COMPARISON WITH PARENTAL AND COMMERCIAL CULTIVARS

'Camp Trailbule' differs from the female parent 'CD-20-1' (unpatented) in that 'Camp Trailbule' has smaller, lighter blue flowers and a more trailing plant habit than 'CD-20-1'.

'Camp Trailbule' differs from the male parent 'CH-60-5' (unpatented) in that 'Camp Trailbule' has larger, deeper blue flowers than 'CH-60-5'. Additionally, 'Camp Trailbule' has a more trailing plant habit, while 'CH-60-5' has a mounding plant habit.

'Camp Trailbule' does not match any commercial variety but differs from *Campanula portenschlagiana* Schult., a trailing species, in that 'Camp Trailbule' has larger, deeper blue flowers and a more vigorous growth habit than *Campanula portenschlagiana* Schult.

I claim:

1. A new and distinct cultivar of *campanula* plant as shown and described herein.

* * * * *